(12) United States Patent
Hansen et al.

(10) Patent No.: US 7,846,724 B2
(45) Date of Patent: Dec. 7, 2010

(54) METHOD FOR SELECTING CHO CELL FOR PRODUCTION OF GLYCOSYLATED ANTIBODIES

(75) Inventors: Silke Hansen, Iffeldorf (DE); Klaus-Peter Kuenkele, Benediktbeuern (DE); Dietmar Reusch, Munich (DE); Ralf Schumacher, Penzberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 362 days.

(21) Appl. No.: 11/732,974

(22) Filed: Apr. 5, 2007

(65) Prior Publication Data
US 2007/0248600 A1 Oct. 25, 2007

(30) Foreign Application Priority Data
Apr. 11, 2006 (EP) .................................. 06007565
Aug. 3, 2006 (EP) .................................. 06016203

(51) Int. Cl.
C12N 5/06 (2006.01)
(52) U.S. Cl. ...................................................... 435/326
(58) Field of Classification Search ........................ None
See application file for complete search history.

(56) References Cited

U.S. PATENT DOCUMENTS

| | | | |
|---|---|---|---|
| 5,202,238 A | 4/1993 | Fell et al. | |
| 5,204,244 A | 4/1993 | Fell et al. | |
| 5,610,297 A | 3/1997 | Powers | |
| 5,770,429 A | 6/1998 | Lonberg et al. | |
| 7,432,359 B2 * | 10/2008 | Kataoka et al. | 530/388.15 |
| 2003/0165502 A1 | 9/2003 | Fujita-Yamaguchi | |
| 2004/0018191 A1 | 1/2004 | Wang et al. | |
| 2005/0084906 A1 | 4/2005 | Goetsch et al. | |
| 2005/0249730 A1 | 11/2005 | Goetsch et al. | |
| 2008/0014203 A1 * | 1/2008 | Hansen et al. | 424/158.1 |

FOREIGN PATENT DOCUMENTS

| | | |
|---|---|---|
| EP | 1176195 | 1/2002 |
| WO | WO 87/05330 | 9/1987 |
| WO | 94/11026 | 5/1994 |
| WO | WO 95/14930 | 6/1995 |
| WO | WO 98/22136 | 5/1998 |
| WO | WO 99/51642 | 10/1999 |
| WO | WO 99/54342 | 10/1999 |
| WO | 00/61739 | 10/2000 |
| WO | WO 01/14424 | 3/2001 |
| WO | WO 02/053596 | 7/2002 |
| WO | WO 03/059951 | 7/2003 |
| WO | 03/106621 | 12/2003 |
| WO | WO 03/100008 | 12/2003 |
| WO | 2004/071529 | 8/2004 |
| WO | 2004/083248 | 9/2004 |
| WO | WO 2004/087756 | 10/2004 |
| WO | WO 2005/005635 | 1/2005 |
| WO | 2005/016967 | 2/2005 |
| WO | 2005/016970 | 2/2005 |
| WO | WO 2005/023872 A1 | 3/2005 |
| WO | 2005/058967 | 6/2005 |
| WO | 2005/082415 | 9/2005 |
| WO | 2005/094376 | 10/2005 |
| WO | 2006/008639 | 1/2006 |
| WO | 2006/013472 | 2/2006 |

OTHER PUBLICATIONS

Boerner et al., J. Immunol., 147, pp. 86-95 (1991).
Bruggemann et al., Year Immunol., 7, pp. 33-40 (1993).
Cole et al., Monoclonal Antibodies and Cancer Therapy, Alan R. Liss, pp. 77 (1985).
Hoogenboom et al., J. Mol. Biol., 227, pp. 381-388 (1992).
Jakobovits et al., Nature, 362, pp. 255-258 (1993).
Jakobovits et al., Proc. Natl. Acad. Sci, USA, 90, pp. 2551-2555 (1993).
Johnson et al., Nucleic Acids Res., 28, pp. 214-218 (2000).
Kane et al., Gene, 84, pp. 439-446 (1989).
Kolkekar et al., Biochemistry, 36, pp. 10901-10909 (197).
Makrides, S.C., Protein Expr. Purif., 17, pp. 183-202 (1999).
Marks et al., J. Mol. Biol., 222, pp. 581-597 (1991).
Mori, T., Biotech. Bioeng., 88, pp. 901-908 (2004).
Morrison et al., Proc. Natl. Acad. Sci. USA, 81, pp. 6851-6855 (1984).
Neuberger et al., Nature, 314, pp. 268-270 (1985).
Thelander et al., EMBO J., 8, pp. 2475-2479 (1989).
Urlaub et al., Cell, 33, pp. 405-412 (1983).
Urlaub et al., Somat. Cell Mol., Genet., 12, pp. 555-566 (1986).
Van Dijk et al., Curr. Opin. Chem. Biol., 5, pp. 368-374 (2001).
Werner, R.G., Drug Res., 48, pp. 870-880 (1998).
U.S. Appl. No. 11/784,029, Office Action dated Aug. 6, 2008.
U.S. Appl. No. 11/784,029, Office Action dated Mar. 18, 2009.
Ito et al., J. Virol., 74, pp. 9300-9305 (2000).
Stabila et al., Nature Biotech, 16, pp. 1357-1360 (1998).
Routier et al., Glycoconjugate J., 14, pp. 201-207 (1997).
Niwa et al., J. Immunol. Methods, 306, pp. 151-160 (2005).
Mimura et al., J. Immunol Methods, 247, pp. 205-216 (2001).
Raju, T.S., BioProcess International, 1, pp. 44-53 (2003).
Ma, S., Anal. Chem., 71, pp. 5185-5192 (1999).
Fujii, S., J. Biol. Chem., 265, pp. 6009-6018 (1990).

(Continued)

Primary Examiner—Michail A Belyavskyi
(74) Attorney, Agent, or Firm—George W. Johnston; Patricia S. Rocha-Tramaloni; David E. Wildman

(57) ABSTRACT

The invention provides an antibody comprising human IgG1 or IgG3 heavy chain constant domains that are glycosylated with a sugar chain at Asn297, said antibody being characterized in that the amount of fucose within said sugar chain is at least 99%, and in addition the amount of NGNA is 1% or less and/or the amount of N-terminal alpha 1,3 galactose is 1% or less, and uses thereof.

1 Claim, 1 Drawing Sheet

OTHER PUBLICATIONS

Mizouchi et al., J. Immunol., 129, pp. 2016-2020 (1982).
Bergwerff et al., Glycoconjugate J., 12, pp. 318-330 (1995).
Nahrgang et al., Animal Cell Technology: Products from Cells, Cells as Products, Bernard et al. (eds), Kluwer Academic Publishers, Dordrecht, NL, pp. 259-261 (1999).
Lund et al., Mol. Immuno., 30, pp. 741-748 (1993).
Patel et al., Biochem. J., 285, pp. 839-845 (1992).
Davies et al., Biotechnol. Bioeng., 74, pp. 288-294 (2001).
Sheeley et al., Anal. Biochem, 247, pp. 102-110 (1997).
Shields et al., J. Biol. Chem., 277, pp. 26733-26740 (2002).
Zhu et al., Nature Biotechnol., 23, pp. 1159-1169 (2005).
Wright et al., Trends Biotechnol., 15, pp. 26-32 (1997).
Lifely et al., Glycobiology, 5, pp. 813-822 (1995).
Jefferis et al., Immunol. Rev., 163, pp. 59-76 (1998).
Bowie et al., Science, 247, pp. 1306-1310 (1990).
Flintoff et al., Somat. Cell Genet., 2, pp. 245-261 (1976).
Flintoff et al., Mol. Cell. Biol., 2, pp. 276-285 (1982).
Li et al., Cancer Immunology and Immunotherapy, 49, pp. 243-252, XP001113064 (2000).
Lubeck et al, The Journal of Immunology, 135(2), pp. 1299-1304 (1985).
Adams et al., Cell. Mol. Life Sci., 57, pp. 1050-1093 (2000).
Brüggemann et al., J. Exp. Med., 166, pp. 1351-1361 (1987).
Chen et al., EMBO J., 12, pp. 821-830 (1993).
Fishwild et al., Nat. Biotechnol., 14, pp. 845-851 (1996).
Lonberg et al., Nature, 368, pp. 856-859 (1994).
Love et al., Methods Enzymol., 178, pp. 515-527 (1989).
Riechmann et al., Nature, 332, pp. 323-327 (1988).
Schlaeger et al., Cytotechnology, 30, pp. 71-83 (1999).
Wilman, D.E.V., Prodrugs in Cancer Chemotherapy Biochemical Society Transactions, 14, pp. 375-383, 615th Meeting Belfast (1986).
Rohlik et al., Biochemical and Biophysical Research Communications, vol. 149, No. 1, pp. 276-281 (1987), XP008026319.
Hailey et al., Molecular Cancer Therapeutics, 1, pp. 1349-1353 (2002), XP008026465.
Pietrzkowski et al., Cell Growth Differ., 3, pp. 199-205 (1992).
Schnitzer, et al., European Journal of Cancer, Supplement, Pergamon, Oxford, GB, vol. 4, No. 12 (2006), XP005810433.
Benini, S., et al., Clin. Cancer Res., 7, pp. 1790-1797 (2001).
Bergmann, U., et al., Cancer Res., 55, pp. 2007-2011 (1995).
Brunetti, A., et al., Biochem. Biophys. Res. Commun., 165, pp. 212-218 (1989).
Delafontaine, P., et al., J. Mol. Cell. Cardiol., 26, pp. 1659-1673 (1994).
Dricu, A., et al., Glycobiology, 9, pp. 571-579 (1999).
Forsayeth, J. R., et al., Proc. Natl. Acad. Sci. USA, 84, pp. 3448-3451 (1987).
Gustafson, T. A., and Rutter, W. J., J. Biol. Chem., 265, pp. 18663-18667 (1990).
Hoyne, P. A., et al., FEBS Lett., 469, pp. 57-60 (2000).
Kalebic, T., et al., Cancer Res., 54, pp. 5531-5534 (1994).
Kanter-Lewensohn, L., et al., Melanoma Res., 8, pp. 389-397 (1998).
Kato, H., et al., J. Biol. Chem., 268, pp. 2655-2661 (1993).
Kull, F. C., J. Biol. Chem., 258, pp. 6561-6566 (1983).
Lammers, R., et al., EMBO J., 8, pp. 1369-1375 (1989).
Li, S. L., et al., Biochem. Biophys. Res. Commun., 196, pp. 92-98 (1993).
Morgan, D. O., and Roth, R. A., Biochemistry, 25, pp. 1364-1371 (1986).
O'Brien, R. M., et al., EMBO J., 6, pp. 4003-4010 (1987).
Pessino, A., et al., Biochem. Biophys. Res. Commun., 162, pp. 1236-1243 (1989).
Prigent, S. A., et al., J. Biol. Chem., 265, pp. 9970-9977 (1990).
Schaefer, E. M., et al., Biol. Chem., 265, pp. 13248-13253 (1990).
Scotlandi, K., et al., Cancer Gene Ther., 9, pp. 296-307 (2002).
Scotlandi, K., et al., Int. J. Cancer, 101, pp. 11-16 (2002).
Soos, M. A., et al., Proc. Natl. Acad. Sci. USA, 86, pp. 5217-5221 (1989).
Stella, V. J., et al., "Prodrugs: A Chemical Approach to Targeted Drug Delivery," In: Directed Drug Delivery, Borchardt, R. T., et al., (eds.), pp. 247-267, Humana Press, Clifton, New Jersey (1985).
Surinya, K. H., et al., J. Biol. Chem., pp. 16718-16725 (2002).
Taylor, R., et al., Biochem. J., 242, pp. 123-129 (1987).
Tulloch, P. A., et al., J. Struct. Biol., 125, pp. 11-18 (1999).

* cited by examiner

METHOD FOR SELECTING CHO CELL FOR PRODUCTION OF GLYCOSYLATED ANTIBODIES

PRIORITY TO RELATED APPLICATIONS

This application claims the benefit of European Application Nos. 06007565.2, filed Apr. 11, 2006, and 06016203.9, filed Aug. 3, 2006, which are hereby incorporated by reference.

The present invention relates to a recombinant antibody having an Fc region expressed and glycosylated, whereby a major core carbohydrate structure attached to the Fc region of the antibody is fully fucosylated. The present invention relates also to CHO (chinese hamster ovary) host cells, methods for selecting such CHO host cells and the use of such a recombinant antibody.

BACKGROUND OF THE INVENTION

Immunoglobulins or antibodies in their native form are usually tetrameric glycoproteins composed of two light and two heavy chains. Antibodies contain constant domains which assign the antibodies to different classes like IgA, IgD, IgE, IgM, and IgG, and several subclasses like IgG1, IgG2, IgG3, and IgG4. Antibodies of humans of class IgG1 and IgG3 usually mediate ADCC (antibody-dependent cell-mediated cytotoxicity).

There are also known other molecules which are antibody-like and contain, for example, a binding domain of a heterologous protein such as a receptor, ligand or enzyme, and the Fc region of an antibody. Such Fc fusion proteins are described, for example, by Stabila, P., et al., Nature Biotech 16 (1998) 1357-1360 and U.S. Pat. No. 5,610,297.

Monoclonal antibodies elicit four effector functions: ADCC, phagocytosis, complement-dependent cytotoxicity (CDC) and half-life/clearance rate. ADCC and phagocytosis are mediated through the interaction of cell-bound antibodies with FcγR (Fc gamma receptors); CDC through the interaction of cell-bound antibodies with a series of proteins that constitute the complement system. CDC is related to C1q binding C3 activation and/or Fc receptor binding of the Fc part. If C1q binding C3 activation and/or Fc receptor binding of an antibody constant part should be reduced, usually IgG4 antibodies are used which do not activate the complement system, do not bind C1q and do not activate C3. Alternatively, Fc parts comprising a gamma-1 heavy chain constant region with certain mutations such as L234A and L235A or D265A and N297A (WO 99/51642) are used.

It is well-known in the state of the art to modify the constant domains of antibodies for improving effector functions. Such methods are described, for example, in WO 99/54342.

Routier, F. H. et al., Glycoconjugate J. 14 (1997) 201-207 report the glycosylation pattern of a humanized IgG1 antibody expressed in CHO-DUKX cells. This antibody shows a molar ratio of Fuc:Man of 0.8:3.0, which refers to a fucosylation ratio of 80%. Niwa, R. et al., J. Immunol. Methods 306 (2005) 151-160 report for anti-CD20 IgG1 and IgG3 antibodies recombinantly produced in CHO DG44 fucosylation of about 90%. Mimura, Y et al., J. Immunol. Methods 247 (2001) 205-216 report that butyrate increases production of human chimeric IgG in CHO-K1 cells whilst maintaining function and glycoform profile. The oligosaccharide profiles show a considerable content of afucosylated glycan structures. Raju, T. S., BioProcess International 1 (2003) 44-53 report the impact of glycosylation variation by expression systems on the biological activity of therapeutic immunoglobulins and the nomenclature. Ma, S., Anal. Chem. 71 (1999) 5185-5192 report the carbohydrate analysis of rituximab. Rituximab shows 9-10% fucosylation (Niwa, R. et al., J. Immunol. Methods 306 (2005) 151-160). Fujii, S., J. Biol. Chem. 265 (1990) 6009-6018 report that bovine IgG includes about 11% afucosylated IgG. Mizouchi, T., J. Immunol. 129 (1982) 2016-2020 report that human IgG is about 14% afucosylated. Bergwerff, A. A., Glycoconjugate J. 12 (1995) 318-330 report that antibodies produced in mouse SP2/0 contains N-glycolylneuraminic acid (NGNA) oligosaccharides in large amounts. Nahrgang, S. et al., In: Animal Cell Technology: Products from Cells, Cells as Products, Bernard, A. et al. (eds.), Kluwer Academic Publishers, Dordrecht, N L, 1999, pp. 259-261, report that for CHO expression of IgG1 after transient transfection a poor overall glycosylation is found. Lund, J. et al., Mol. Immunol. 30 (1993) 741-748 report recombinant production of a mouse-human chimeric antibody in mouse transfectoma cells. The IgG1 antibody is afucosylated in an amount of 13%. Patel, T. P. et al., Biochem. J. 285 (1992) 839-845 report on glycosylation of antibodies from hybridoma cells and mouse ascites. Niwa, R. et al., J. Immunol. Methods 306 (2005) 151-160, report for CD20 IgG1 antibody a fucosylation of 91% after recombinant production in CHO DG44 and Mori, K. et al., Biotech. Bioeng. 88 (2004) 901-908, a fucosylation of 94%. Davies, J., et al., Biotechnol. Bioeng. 74 (2001) 288-294 report that expression of antibodies with altered glycoforms leads to an increase of ADCC. Sheeley, D. M., et al., Anal. Biochem. 247 (1997) 102-110 compare antibody glycosylation in different expression systems. Shields, R. L., et al., J. Biol. Chem. 277 (2002) 26733-26740 report that lack of fucose on human IgG1 Fc improves FcγRIII binding and ADCC. An anti Her2 antibody being about 90% fucosylated shows also ADCC in a considerable amount. Zhu, L., et al., Nature Biotechnol. 23 (2005) 1159-1169 report on the production of human antibodies in chicken eggs. WO 2004/087756 and WO 2005/005635 disclose improved antibodies against IGF-1R.

SUMMARY OF THE INVENTION

The invention comprises an antibody of human IgG1 or IgG3 type being glycosylated with a sugar chain at Asn297, said antibody being characterized in that the amount of fucose within said sugar chain is at least 99%, and in addition the amount of NGNA is 1% or less and/or the amount of N-terminal alpha-1,3-galactose is 1% or less.

According to the invention "amount" means the amount of said sugar within the sugar chain at Asn297, related to the sum of G0, G1, G2 (without mannose (4 and 5) as 100% and as calculated in example 3.

According to the invention it is possible to provide antibodies and/or CHO host cells with a fucosylation of even 99.4% or more, 99.5% or more or 99.9% or more.

Preferably the amount of NGNA is 0.5% or less, more preferably 0.1% or less and even not detectable by LCMS (Liquid Chromatography/Mass Spectrometry).

Preferably the amount of N-terminal alpha 1,3 galactose is 0.5% or less, more preferably 0.1% or less and even not detectable by LCMS.

The sugar chain show preferably the characteristics of N-linked glycans attached to Asn297 of an antibody recombinantly expressed in a CHO cell.

Preferably the antibody is a monoclonal antibody. Preferably the antibody is a chimeric, humanized or human antibody.

The invention further comprises a CHO cell capable of recombinantly expressing an antibody of human IgG1 or IgG3 type being glycosylated with a sugar chain at Asn297, said antibody being characterized in that within said sugar chain the amount of fucose is at least 99%, and in addition the amount of NGNA is 1% or less and/or the amount of N-terminal alpha 1,3 galactose is 1% or less.

Such a cell line is cell line hu MAb<IGF-1R>B1-4E10_ 9-16) deposited under the Budapest Treaty on the international recognition of the deposit of microorganisms for the purposes of patent procedure, with Deutsche Sammlung von Mikroorganismen und Zellkulturen GmbH (DSMZ), Germany, on Jun. 21, 2006 under Accession No. DSM ACC 2795.

Preferred sugar amounts are mentioned above.

Preferably the CHO cell is a CHO cell comprising deletion (e.g. DG44) or functional inactivation of both DHFR alleles or a deletion of one DHFR allel and a functional inactivation of the second DHFR allel (e.g. DXB11).

The invention further comprises a composition according to the invention for use in human medical therapy.

The antibody of the composition according to the invention is preferably a chimeric antibody, a human antibody, a humanized antibody, a non-human antibody, a single chain antibody comprising IgG1 or IgG3 heavy chain constant part, or a IgG1 or IgG3 heavy chain constant part.

The invention further comprises the use of an antibody according to the invention for the manufacture of a medicament. Preferably the medicament is useful for immunosuppression for the treatment of T-cell mediated disorders, autoimmune disorders, infectious diseases, cancer diseases.

The invention further comprises a pharmaceutical composition comprising an antibody according to the invention.

A further object of the invention is a method for the selection of a CHO cell for the recombinant production of a monoclonal antibody of human IgG1 or IgG3 type being glycosylated with a sugar chain at Asn297, said antibody being characterized in that the amount of fucose within said sugar chain is at least 99%, and in addition the amount of NGNA is 1% or less and/or the amount of N-terminal alpha 1,3 galactose is 1% or less, said method comprising cultivating a CHO cell, transfected with an IgG1 or IgG3 antibody and a DHFR gene, under DHFR and MTX selection pressure, picking single clones expanding the clones and selecting a done producing an antibody with the glycosylation pattern according to the invention. Preferably cultivation is performed for at least two, preferably at least three weeks.

A further object of the invention is the use of a CHO cell according to the invention for the recombinant production of a monoclonal antibody.

A further object of the invention is a method for the recombinant production of a monoclonal antibody in a CHO cell according to the invention.

The CHO cell is a host cell useful for the recombinant expression of heterologous polypeptides.

DETAILED DESCRIPTION OF THE INVENTION

Figure 1:
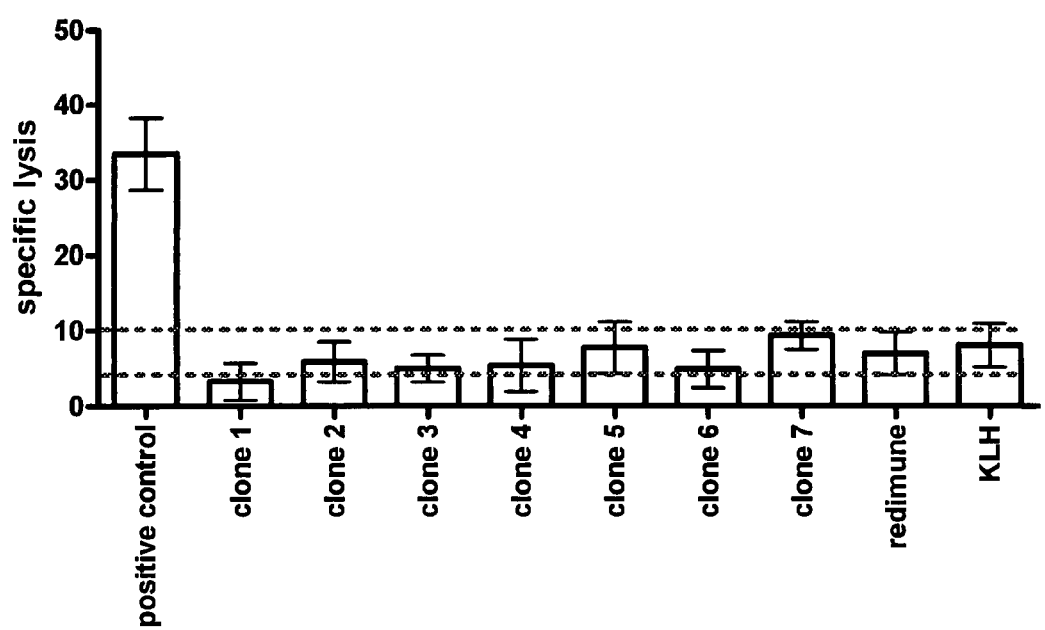
FIG. 1 is a bar chart showing the ADCC activity or lack thereof in antibodies of the invention and in control and comparative antibodies.

Antibodies contain carbohydrate structures at conserved positions in the heavy chain constant regions, with each isotype possessing a distinct array of N-linked carbohydrate structures, which variably affect protein assembly, secretion or functional activity (Wright, A., and Morrison, S. L., Trends Biotechnol. 15 (1997) 26-32). The structure of the attached N-linked carbohydrate varies considerably, depending on the degree of processing, and can include high-mannose, multiply-branched as well as biantennary complex oligosaccharides (Wright, A., and Morrison, S. L., Trends Biotechnol. 15 (1997) 26-32).

Antibodies of IgG1 and IgG3 type are glycoproteins that have a conserved N-linked glycosylation site at Asn297 in each CH2 domain. The two complex bi-antennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC) (Lifely, M. R., et al., Glycobiology 5 (1995) 813-822; Jefferis, R., et al., Immunol Rev. 163 (1998) 59-76; Wright, A. and Morrison, S. L., Trends Biotechnol. 15 (1997) 26-32).

As used herein, the term "Fc region of human IgG type" preferably includes also naturally occurring allelic variants of the Fc region of an immunoglobulin (antibody) as well as variants having alterations which are substitutions, additions, or deletions but which do not affect Ans297 glycosylation. For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, J. U., et al., Science 247 (1990) 1306-1310).

The term "antibody" encompasses the various forms of antibodies including but not being limited to whole antibodies, antibody fragments, human antibodies, humanized antibodies and genetically engineered antibodies as long as the characteristic properties according to the invention are retained. Therefore an antibody according to the invention contains at least a functionally active (FcR binding) Fc part of IgG1 or IgG3 type comprising glycosylated Asn297.

The terms "monoclonal antibody" or "monoclonal antibody composition" as used herein refer to a preparation of antibody molecules of identical amino acid sequence. Accordingly, the term "human monoclonal antibody" refers to antibodies displaying a single binding specificity which have variable and constant regions derived from human germline immunoglobulin sequences.

The term "chimeric antibody" refers to a monoclonal antibody comprising a variable region, i.e., binding region, from one source or species and at least a portion of a constant region derived from a different source or species, usually prepared by recombinant DNA techniques. Chimeric antibodies comprising a murine variable region and a human constant region are especially preferred. Such murine/human chimeric antibodies are the product of expressed immunoglobulin genes comprising DNA segments encoding murine immunoglobulin variable regions and DNA segments encoding human immunoglobulin constant regions. Methods for producing chimeric antibodies involve conventional recombinant DNA and gene transfection techniques now well known in the art (see, e.g., Morrison, S. L., et al., Proc. Natl. Acad. Sci. USA 81 (1984) 6851-6855; U.S. Pat. Nos. 5,202, 238 and 5,204,244).

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody" (see, e.g., Riechmann, L., et al., Nature 332 (1988) 323-327; and Neuberger, M. S., et al., Nature 314 (1985) 268-270). Particularly preferred CDRs correspond to those representing sequences recognizing the antigens noted above for chimeric and bifunctional antibodies.

The term "human antibody", as used herein, is intended to include antibodies having variable and constant regions derived from human germline immunoglobulin sequences. Such regions are described by, e.g., Johnson, G., and Wu, T. T., Nucleic Acids Res. 28 (2000) 214-218 and the databases referenced therein and are useful as long as the properties according to the invention are retained. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g. mice) that are capable, upon immunization, of producing a full repertoire or a selection of human antibodies in the absence of endogenous immunoglobulin production. Transfer of the human germ-line immunoglobulin gene array in such germ-line mutant mice result in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Bruggemann, M., et al., Year Immunol. 7 (1993) 33-40). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole et al. and Boerner et al. are also available for the preparation of human monoclonal antibodies (Cole et al., Monoclonal Antibodies and Cancer Therapy, Alan R. Liss, p. 77 (1985); and Boerner, P., et al., J. Immunol. 147 (1991) 86-95). A human antibody encompasses the various forms of antibodies, preferably monoclonal antibodies including but not being limited to whole antibodies, antibody fragments and genetically engineered antibodies (variant or mutant antibodies) as long as the characteristic properties according to the invention are retained. Especially preferred are recombinant human antibodies.

The term "recombinant human antibody", as used herein, is intended to include all human antibodies that are prepared, expressed, created or isolated by recombinant means, such as antibodies isolated from a host cell according to the invention, using a recombinant expression vector transfected into such a host cell.

The "constant domains" are not involved directly in binding of an antibody to an antigen, but exhibit other functions like effector functions. The heavy chain constant regions that correspond to IgG1 is called γ1 chain. The heavy chain constant regions that correspond to IgG3 is called γ3 chain. Human constant γ heavy chains are described in detail by Kabat, E. A. et al., Sequences of Proteins of Immunological Interest, 5th ed., Public Health Service, National Institutes of Health, Bethesda, Md. (1991), and by Brueggemann, M., et al., J. Exp. Med. 166 (1987) 1351-1361; Love, T. W., et al., Methods Enzymol. 178 (1989) 515-527. Constant domains of IgG1 or IgG3 type are glycosylated at Asn297. "Asn297" according to the invention means amino acid asparagine located at about position 297 in the Fc region; based on minor sequence variations of antibodies, Asn297 can also be located some amino acids (usually not more than ±3 amino acids) upstream or downstream. For example, in one antibody according to the invention "Asn297" is located at amino acid position 298.

Glycosylation of human IgG1 or IgG3 occurs at Asn297 as core fucosylated bianntennary complex oligosaccharide glycosylation terminated with up to 2 Gal (galactose) residues. These structures are designated as G0, G1 ($\alpha$1,6 or $\alpha$1,3) or G2 glycan residues, depending from the amount of terminal Gal residues (Raju, T. S., BioProcess International 1 (2003) 44-53). CHO type glycosylation of antibody Fc parts is e.g. described by Routier, F. H., Glycoconjugate J. 14 (1997) 201-207.

The "variable region" (variable region of a light chain (VL), variable region of a heavy chain (VH)) as used herein denotes each of the pair of light and heavy chains which is involved directly in binding the antibody to the antigen.

According to the invention, an antibody producing CHO host cell can be selected which is able to provide via recombinant expression a composition of a monoclonal antibody showing a glycosylation pattern according to the invention. Such a CHO host cell comprises one or more expression vector(s) for the recombinant expression of such antibody. Preferably the host cell is stable transfected with the vector(s) and the antibody encoding nucleic acids are integrated in to the CHO host cell genome.

The term "CHO cell" encompasses the various forms of Chinese Hamster Ovary (CHO) cells based on two functionally inactivated, preferably deleted, dhfr alleles (dihydrofolate reductase deficient (dhfr⁻)). Such dhfr⁻ cells and methods for their generation are described e.g. in Urlaub, G. et al., Cell 33 (1983) 405-412; Urlaub, G. et al., Som. Cell Molec. Genet. 12 (1986) 555-566; Kolkekar et al., Biochemistry 36 (1997) 10901-10909. Preferably the cell is a DG44 cell line. Such CHO dhfr⁻ cells can be produced using gamma rays to eliminate the entire dhfr locus. In non-mutated, wild-type cells, dhfr is an essential enzyme for de novo synthesis of glycine, purines, and thymidylate. This allows the dhfr gene encoded on plasmids to be used as a dominant selectable marker and a gene amplifier for the expression of proteins in dhfr⁻ deficient cell lines. The dhfr⁻ mutation in DG44 cells is stable and irreversible. CHO cells successfully co-transfected with expression vector(s) for an antibody of human IgG1 or IgG3 type and the DHFR gene will possess the dhfr+ phenotype and can readily be selected by culturing the colonies on media devoid of thymidine and hypoxanthine and optionally containing methotrexate (MTX) for amplification.

DG44 cells are well known in the state of the art and e.g. commercial available as cell lines e.g. from Invitrogen Corp. (USA). DG44 cells can grow adherent, in suspension and/or in serum-free medium. As used herein, the expressions "cell," "cell line," and "cell culture" are used interchangeably and all such designations of CHO dhfr⁻ cell lines (two deleted dhfr alleles) include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the glycosylation properties according to the invention as screened for in the originally transformed cell are included.

Preferably the CHO dhfr⁻ cell line is co-amplified with at least DHFR as one selectable marker gene. For example a mammalian expression vector containing the selectable marker(s) and the antibody gene are co-transfected into recipient CHO cells. The resulting colonies may be selected and colonies exhibiting the expected phenotype are capable of expressing the antibody. Additional selectable markers are or may not be of a dominant nature. Examples of additional selectable markers for use co-transfection include adenosine deaminase (Kaufman, R. J., et al., Proc. Natl. Acad. Sci. USA 83 (1986) 3136-3140) asparagine synthetase (Cartier, M., et al., Mol. Cell Biol. 7 (1987) 1623-1628), *E. coli* trpB gene and *Salmonella* hisD gene (Hartman, S. C., and Mulligan, R. C., Proc. Natl. Acad. Sci. USA 85 (1988) 8047-8051), M2 mouse ribonucleotide reductase (Thelander, M., and Thelander, L., EMBO J. 8 (1989) 2475-2479), human multidrug resistance gene (Kane, S. E., et al., Gene 84 (1989) 439-446), glutamine synthetase (Bebbington, C. R. et al., DNA Cloning, Vol. III, D. M. Glover (ed.), IRL Press, pp. 163-188, 1987), xanthine guanine phosphoribosyl transferase (gpt) (Mulligan, R. C., and Berg, P., Science 209 (1980) 1422-1427), hygromycin B (Santerre, R. F., et al., Gene 30 (1984) 147-156), neomycin gene (Southern, P. J., and Berg, P., J. Mol. Appl. Genet. 1 (1982) 327-341).

The selectable markers may also provide the basis upon which the genes encoding the antibody may be amplified. In co-transfection of a CHO cell line, the vector DNAs are often integrated into the chromosome of the cell at the same locus. Thus, the use of only one of the selectable markers as the basis for amplification normally results in a parallel increase in the copy number of both genes. One particular selectable marker for use in this way is dhfr which enables the desired amplification to be obtained through the use of increasing concentrations of MTX. A second preferred selectable marker is GS which allows amplification by the addition of methionine sulphoximine (MSX).

The selectable markers are of course under the control of regulatory elements of DNA so as to provide for their expression. In the case of the use of dhfr as a selectable marker, the regulatory elements are preferably of a viral source, such as from DNA tumor viruses. Particularly preferred are the use of an SV40 or adenovirus major late promoter. It is particularly advantageous in this regard to remove the enhancer element from the promoter thus effectively "crippling" it. This modification allows for increased levels of gene amplification at each concentration of methotrexate selection than would otherwise occur if a strong promoter was used. In the case of the use of neomycin as a selectable marker, an example of a suitable promoter is the mouse metallothionein promoter.

The term nucleic acid or nucleic acid molecule, as used herein, is intended to include DNA molecules and RNA molecules. A nucleic acid molecule may be single-stranded or double-stranded, but preferably is double-stranded DNA.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are cis, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

The antibodies according to the invention are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression, nucleic acids encoding light and heavy chains or fragments thereof are inserted into expression vectors by standard methods. Expression is performed in CHO host cells and the antibody is recovered from the cells or supernatant preferably after lysis).

Recombinant production of antibodies is well-known in the state of the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-161; Werner, R. G., Drug Res. 48 (1998) 870-880.

The antibodies may be present in whole cells, in the supernant, in a cell lysate, or in a partially purified or substantially pure form. Purification is performed in order to eliminate other cellular components or other contaminants, e.g. other cellular nucleic acids or proteins, by standard techniques, including alkaline/SDS treatment, CsCl banding, column chromatography, agarose gel electrophoresis, and others well known in the art (see Ausubel, F., et al., ed. Current Protocols in Molecular Biology, Greene Publishing and Wiley Interscience, New York (1987)).

The control sequences that are suitable for prokaryotes, for example, include a promoter, optionally an operator sequence, and a ribosome binding site. Eukaryotic cells are known to utilize promoters, enhancers and polyadenylation signals.

The monoclonal antibodies can be suitably separated from a hybridoma culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies is readily isolated from the hybridoma and sequenced using conventional procedures. The hybridoma cells can serve as a source of such DNA and RNA. Once identified and isolated, the DNA may be inserted into expression vectors, which are then transfected into CHO cells that do not otherwise produce immunoglobulin protein, to obtain the synthesis of recombinant monoclonal antibodies in the host cells.

In another aspect, the present invention provides a pharmaceutical composition, comprising a composition of the present invention, formulated together with a pharmaceutically acceptable carrier. Preferably a pharmaceutical composition according to WO 98/22136 is used. Such a composition contains e.g. in 1 ml 2.0 mg antibody, 15 mM phosphate buffer pH6.5, 30 mM sodium chloride, 25 mg mannite, arginine 10 mg, 0.1 mg Tween®20.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

A "pharmaceutically acceptable salt" refers to a salt that retains the desired biological activity of the antibody and does not impart any undesired toxicological effects (see e.g. Berge, S. M., et al., J. Pharm. Sci. 66 (1977) 1-19). Such salts are included in the invention. Examples of such salts include acid addition salts and base addition salts. Acid addition salts include those derived from nontoxic inorganic acids, such as hydrochloric salts.

A composition of the present invention can be administered by a variety of methods known in the art. As will be appreciated by the skilled artisan, the route and/or mode of administration will vary depending upon the desired results.

To administer a compound of the invention by certain routes of administration, it may be necessary to coat the compound with or coadminister the compound with, a material to prevent its inactivation. For example, the compound may be administered to a subject in an appropriate carrier, for example, liposomes, or a diluent. Pharmaceutically acceptable diluents include saline and aqueous buffer solutions.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier can be an isotonic buffered saline solution, ethanol, polyol (for example, glycerol, propylene glycol, and liquid polyethylene glycol, and the like), and suitable mixtures thereof.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

The following examples and the FIGURE are provided to aid the understanding of the present invention, the true scope of which is set forth in the appended claims. It is understood that modifications can be made in the procedures set forth without departing from the spirit of the invention.

EXAMPLES

Cell Lines

The parental cell line used for the generation of a cell line for recombinant IgG expression is a Chinese hamster ovarian (CHO) cell line, CHO-DG44 (Flintoff, W. F. et al., Somat. Cell Genet. 2 (1976) 245-261; Flintoff, W. F. et al., Mol. Cell. Biol. 2 (1982) 275-285; Urlaub, G. et al., Cell 33 (1983) 405-412; Urlaub. G. et al., Somat. Cell Mol. Genet. 12 (1986) 555-566). CHO-DG44 cells have lost both endogenous loci for the enzyme Dihydrofolate Reductase (DHFR).

CHO-DG44 cells were grown in MEM alpha Minus Medium (Gibco No. 22561), 10% dialysed FCS (Gibco No. 26400-044) and 2 mmol/L L-Glutamine, 100 µM Hypoxanthin, 16 µM Thymidin (HT supplement).

Plasmids

The expression system comprised the CMV promoter and is described in table 1. As antibody an antibody against IGF-1R (WO2005005635; AK18 or AK22) was used.

TABLE 1

| Bp | Vector element/DNA segment |
|---|---|
| 1-26 | Unique restriction sites: SgrAI, Sse83871 |
| 27-614 | Human cytomegalovirus (HCMV) promoter (CMV-Prom) including human CMV IE promoter including synthetic 5'-UTR |
| 615-641 | Linker |
| 642-780 | Murine Ig heavy chain leader sequence (L1, signal sequence intron, L2) |
| 642-686 | L1 |
| 687-768 | Signal intron (SS intron) |
| 769-780 | L2 |
| 781-1105 | Variable κ-light chain domain of IGF-1R antibody (AK18) |
| 1106-1140 | Linker |
| 1141-3134 | Human/mouse κ-light chain hybrid intron 2 |
| 2433-2913 | κ-enhancer fragment |
| 3135-3475 | Linker |
| 3476-3795 | κ-Light chain constant region (C-kappa) |
| 3796-4098 | Human Ig κ-light chain polyadenylation sequence (C-kappa pA) |
| 4099-4137 | Linker |
| 4138-5800 | Hygromycin resistance |
| 4138-4485 | SV40 promoter (SV40 Prom) incl. 72 bp repeat, TATA, SV40 origin |
| 4486-4502 | Linker |
| 5403-5528 | Hygromycin-B-phosphotransferase (Hyg) |
| 5529-5535 | Linker |
| 5536-5795 | SV40 polyadenylation signal (SV40 pA) |
| 5796-5800 | Linker |
| 5801-6944 | Murine dihydrofolate reductase (DHFR) |
| 5801-6088 | SV40 promoter (SV40 Prom) incl. 72 bp repeat shortened, SV40 origin |
| 6089-6105 | Linker |
| 6106-6672 | Murine DHFR gene (murine DHFR) |
| 6673-6679 | Linker |
| 6680-6944 | SV40 polyadenylation signal (SV40 pA) |
| 6945-7181 | Linker |
| 7182-8941 | Bacterial origin of replication and selective marker derived from plasmid pUC18 |
| 7182-7792 | Origin of replication ("pUC origin") |
| 7793-7939 | Linker |
| 7940-8847 | β-Lactamase gene (Ap(r)) |
| 8848-8941 | Linker |
| 8942-9529 | Human cytomegalovirus (HCMV) promoter (CMV-Prom) including human CMV IE promoter including synthetic 5'-UTR |
| 9530-9556 | Linker |
| 9557-9696 | Murine Ig heavy chain leader sequence (L1, signal sequence intron, L2) |
| 9557-9602 | L1 |
| 9603-9685 | Signal intron (SS intron) |
| 9686-9696 | L2 |

TABLE 1-continued

| Bp | Vector element/DNA segment |
|---|---|
| 9697-10051 | Variable IgG1 heavy chain domain of IGF-1R antibody (AK18) |
| 10052-10085 | Linker |
| 10086-11682 | Human/mouse heavy chain hybrid intron 2 including the part of the mouse Ig heavy chain J-segment region including the Ig heavy chain enhancer element (part $JH_3$, $JH_4$) Mouse Ig heavy chain enhancer element |
| 11683-11909 | Linker |
| 11910-13504 | Human IgG1 heavy chain constant region ($CH_1$-Hinge-$CH_2$—$CH_3$) |
| 11910-12203 | CH1 |
| 12594-12638 | Hinge |
| 12757-13086 | CH2 |
| 13184-13504 | CH3 (alternative splice site deleted) |
| 13505-13967 | Human IgG1 heavy chain polyadenylation sequence (IgG1 pA) |
| 13968-13970 | SgrAI-Linker |

Example 1

Transfection and Selection

Transfection of the expression plasmid was carried out with Fugene (Roche Diagnostics GmbH). A day after transfection, DG44 cells were put under selection pressure consisting of MEM alpha Minus Medium, 10% dialysed FCS and 2 mmol/L L-Glutamine and 20 nM Methotrexate (MTX). After 3 weeks under selection pressure, single clones were picked from the plate and expanded. Supernatants were collected and the presence of the antibody was analyzed with a human IgG-specific ELISA. Subclones were further expanded and analyzed for specific antibody production. Clones were adapted to growth in suspension culture and serum-free medium, HyQ SFM4 CHO-Utility (HyClone #SH30516) containing 20 nM MTX. In parallel, the glyco-pattern profile was determined. Subclones were selected providing defucosylation of 2.0% or lower (referring to total molar oligosaccharide amount).

Example 2

Cultivation and Purification $3 \times 10^5$ cells/ml were grown in 125 ml shake flasks (Corning) filled with 30 ml medium at 37° C., 5% CO2, 100 rpm for 10 days. Cell density was measured by CASY Counter and supernatant was taken for determination of antibody concentration by protein A affinity chromatography. About 20 ml of each supernatant was purified for further biochemical characterization by Protein A chromatography (equilibration with PBS, wash with 25 mM sodiumcitrate buffer pH 5.2, elution with 100 mM sodiumcitrate buffer pH 2.8, CIP with 10 mM NaOH).

Example 3

Analysis of Glycostructure of Antibody

Purified antibody material was analyzed by Liquid Chromatography/Mass Spectrometry (LCMS) Peptide map analysis. Samples were reduced (0.4M TRIS/HCl, 8M Guanidine/HCl, pH 8.5, DTT (3 mg/ml), carboxymethylated (iodoacetic acid) and cleaved with trypsin. The peptide—glycopeptide mixture was separated with RP-HPLC and analysed online with electrospray mass spectrometry. The m/z spectra of the glycostructure containing peptide were integrated, the results are given in Table 2.

TABLE 2

| | Relative amount of glycosylation variants | | | | |
|---|---|---|---|---|---|
| Clone No. | G0 [%] | G1 [%] | G2 [%] | NonFuc[%] | Man[1] [%] |
| 1 | 38.4 | 51.4 | 10.2 | 0.1 | 0.5 |
| 2 | 44.3 | 47.6 | 8.1 | 0.1 | 0.6 |
| 3 | 42.8 | 48.7 | 8.5 | 0.2 | 0.8 |
| 4 | 49.2 | 43.6 | 7.2 | 0.3 | 1.2 |
| 5 | 62.7 | 33.0 | 4.3 | 0.6 | 1.0 |
| 6 | 60.4 | 35.5 | 4.2 | 0.5 | 1.2 |
| 7 | 40.4 | 49.8 | 9.8 | 0.3 | 0.6 |
| 8 | 46.9 | 45.9 | 7.3 | 0.3 | 1.1 |

Man: High Mannose structures bearing four and five mannose residues respectively.

G0, G1, G2: reduced heavy chains with fucosylated biantennary complex type carbohydrate with 1, 2 or 3 terminal galactose residues.

nonFuc: reduced heavy chaina with biantennary complex type carbohydrate without fucose.

The CHO cell line clone 5 (hu MAb<IGF-1R>B1-4E10_9-16) was deposited, under the Budapest Treaty on the international recognition of the deposit of microorganisms for the purposes of patent procedure, with Deutsche Sammlung von Mikroorganismen und Zellkulturen GmbH (DSMZ), Germany, on Jun. 21, 2006 under Accession No. DSM ACC 2795.

The media used for cultivation of the different clones were obtained from Hyclone (HyQ SFM4 CHO-Utility, used for clone 4-6) or Sigma (C-8862, used for done 1-3 and 7). LCMS peptide map analysis was performed by integration of the specific ion chromatograms of all charge states for all glycopeptides.

Bisecting GlcNac, NGNA und high mannose were determined in same manor.

Bisecting GlcNac and NGNA were not detectable. Bisecting GlcNac and NGNA are not detectable, thus the amount of NGNA is 0.5% or lower, and is also 0.1% or lower. The amount of bisecting GlcNAc is also 0.5% or lower, and 0.1% or lower.

An exemplary calculation of glycosylation (clone 3) is shown in table 3 (table 3a: clone 3, table 3b: clone 5; peptide comprising asn298, named H27).

TABLE 3a

| | Area z = 2 | Area z = 3 | Area z = 4 | Sum | rel. amount % |
|---|---|---|---|---|---|
| H27_G0 | 616 | 198 | 0 | 814 | 28.7 |
| H27_G1 | 734 | 425 | 0 | 1158 | 40.9 |
| H27_G2 | 103 | 135 | 0 | 238 | 8.4 |
| H27_G3 | 0 | 0 | 0 | 0 | 0.0 |
| H27_G4 | 0 | 0 | 0 | 0 | 0.0 |
| H27_G1_1NGNA | 0 | 0 | 0 | 0 | 0.0 |
| H27_G2_1NGNA | 0 | 0 | 0 | 0 | 0.0 |
| H27_G2_2NGNA | 0 | 0 | 0 | 0 | 0.0 |
| H27_G3_1NGNA | 0 | 0 | 0 | 0 | 0.0 |
| H27_G3_2NGNA | 0 | 0 | 0 | 0 | 0.0 |
| G0 minus GlcNAc and minus Man | 0 | 57 | 0 | 57 | 2.0 |
| G0 minus GlcNAc | 330 | 0 | 0 | 330 | 11.7 |
| G1 minus GlcNAc | 208 | 0 | 0 | 208 | 7.4 |
| Man5 | 22 | 0 | 0 | 22 | 0.8 |
| G0 minus Fuc | 5 | 0 | 0 | 5 | 0.2 |
| G1 minus Fuc | 0 | 0 | 0 | 0 | 0.0 |
| Man4 | 0 | 0 | 0 | 0 | 0.0 |
| Total | | | | 2833.15 | 100.00 |
| rel. amount of glycostructures with NGNA | | | | | 0.0 |
| rel. amount of glycostructures with Galactoses (G3 und G4) | | | | | 0.0 |

TABLE 3a-continued

| | |
|---|---|
| rel. amount of high mannose | 0.8 |
| Rel. amount of G0 minus Fuc and G1 minus Fuc | 0.2 |
| Sum G0 | 42.4 |
| Sum G1 | 48.2 |
| Sum G2 | 8.4 |
| Total Sum Related to 100% G0-1-2 | 99.0 |
| G0 | 42.8 |
| G1 | 48.7 |
| G2 | 8.5 |
| Sum without Man | 99.2 |
| Sum G0/1 minus Fuc | 0.2 |
| Relative amount without Fuc | 0.2 |

Area: peak area

H27_G0—H27_G4: Glycopeptide H27 (containing Asn 298) with fucosylated biantennary complex type carbohydrate with x-terminal galactose (e.g. G4 with 4 galactose units)

Relative amount without Fuc: percentage of Fuc related to all G0, G1, G2 without mannose (4 and 5) glycostructure (high mannose).

H27_G1__1NGNA—H27_G3__2NGNA: Glycopeptide H27 containing Asn 298) with fucosylated biantennary complex type carbohydrate with x-terminal galactose units (e.g. G2 with 2 units) bearing one to two N-glycolyl-neuraminic acids.

TABLE 3b

Exemplary calculation of glycosylation (clone5)

| | Area z = 2 | Area z = 3 | Area z = 4 | Sum | rel. amount [%] |
|---|---|---|---|---|---|
| G0[1] | 1108 | 318 | 0 | 1426 | 43.8 |
| G1[1] | 579 | 319 | 0 | 897 | 27.6 |
| G2[1] | 67 | 71 | 0 | 139 | 4.3 |
| G3[1] | 0 | 0 | 0 | 0 | 0.0 |
| G4[1] | 0 | 0 | 0 | 0 | 0.0 |
| G1__1NGNA[2] | 0 | 0 | 0 | 0 | 0.0 |
| G2__1NGNA[2] | 0 | 0 | 0 | 0 | 0.0 |
| G2__2NGNA[2] | 0 | 0 | 0 | 0 | 0.0 |
| G3__1NGNA[2] | 0 | 0 | 0 | 0 | 0.0 |
| G3__2NGNA[2] | 0 | 0 | 0 | 0 | 0.0 |
| G0-GlcNAc-Man[3] | 0 | 95 | 0 | 95 | 2.9 |
| G0-GlcNAc[3] | 485 | 0 | 0 | 485 | 14.9 |
| G1-GlcNAc[3] | 159 | 0 | 0 | 159 | 4.9 |
| Man5[4] | 32 | 0 | 0 | 32 | 1.0 |
| G0-Fuc[5] | 11 | 0 | 0 | 11 | 0.3 |
| G1-Fuc[5] | 9 | 0 | 0 | 9 | 0.3 |
| Man4[4] | 0 | 0 | 0 | 0 | 0.0 |
| Total | | | | 3253.88 | 100.00 |
| G0 | | | | | 62.7 |
| G1 | | | | | 33.0 |
| G2 | | | | | 4.3 |
| glycostructures without fucose | | | | | 0.6 |
| glycostructures bearing NGNA | | | | | 0.0 |
| glycostructures bearing additional hexoses (G3 + G4) | | | | | 0.0 |
| high mannose glycostructures | | | | | 1.0 |

[1] fucosylated biantennary complex type glycostructure with x-terminal galactose (0, 1, 2, 3 and 4 respectively)
[2] fucosylated biantennary complex type glycostructure with x-terminal galactose (0, 1, 2, 3 and 4 respectively) with additional n-glycolyl neuraminic acid residues
[3] fucosylated biantennary complex type glycostructures (mainly artefacts of the method)
[4] high Mannose structures bearing four or five mannose residues respectively
[5] non-fucosylated glycostructures Example 4

Determination of Antibody Mediated Effector Functions by Anti-IGF-IR HuMAbs

In order to determine the capacity of the generated HuMAb antibodies to elicit immune effector mechanisms, antibody-dependent cell cytotoxicity (ADCC) studies were performed. To study the effects of the antibodies in ADCC, DU145 prostate cancer cells (HTB-81; $1 \times 10^6$ in 2 to 4 ml RPMI-FM) expressing IGF-IR were labeled with 1 µl bis(acetoxymethyl) 2,2':6',2"-terpyridine-6,6"-dicarboxylate (BATDA) solution for 25 minutes at 37° C. in a cell incubator. Cells were washed four times with 10 ml of RPMI-FM and spun for 10 minutes at 200×g with brake. Afterwards, cells were adjusted to a concentrations of $1 \times 10^5$ cells per ml. 5,000 cells were plated per well in a round bottom plate corresponding to a volume of 50 µl. HuMAb antibodies were added at a final concentration ranging from 25-0.1 ng/ml in a volume of 50 µl cell culture medium. Subsequently, 50 µl of effector cells, PBMC freshly isolated from whole blood or purified effector cells from buffycoats, were added at an E:T ratio in the range of 25:1. The plates were centrifuged immediately for 1 minute at 200×g with brake, and incubated for 2 hours at 37° C. After incubation the cells were spun down for 10 minutes at 200×g and 20 µl of supernatant were transferred to an Optiplate 96-F microtiterplate. 200 µl of Europium solution (at room temperature) were added and the mixture was incubated for 15 minutes on a shaker. Resulting fluorescence was measured in a time-resolved fluorometer using the EU-TDA protocol from Perkin Elmer.

The magnitude of cell lysis by ADCC is expressed as % of the maximum release of 2,2':6',2"-terpyridine-6,6"-dicarboxylate (TDA) from the target cells lysed by detergent corrected for spontaneous release of TDA from the respective target cells. As reference standard of an antibody showing "no ADCC" is used an (monoclonal) antibody against KLH (keyhole limpet hemocyanin) or an IgG mixture isolated from about 35.000 donors ("Redimune"). A 75% fucose free antibody against IGF-IR was used as positive control. An antibody according to the invention showed a TDA release which is within 3×SD of the TDA release of the standard antibody (FIG. 1).

What is claimed is:

1. A method for the selection of a CHO cell that recombinantly produces a monoclonal antibody comprising human IgG1 or IgG3 heavy chain constant domains, wherein the heavy chain constant domains are glycosylated with a sugar chain at Asn297, wherein the sugar chain comprises at least 99% fucose, wherein if the sugar chain comprises N-glycolylneuraminic acid then the amount of N-glycolylneuraminic acid is 1% or less of the sugar chain and wherein if the sugar chain comprises N-terminal alpha-1,3-galactose then the amount of N-terminal alpha-1,3-galactose is 1% or less of the sugar chain;

the method comprising:
(1) cultivating a CHO cell transfected with an expression vector that encodes the heavy and light chains of a monoclonal antibody comprising human IgG1 or IgG3 heavy chain constant domains, wherein two DHFR alleles are deleted from the genome of the CHO cell;
(2) applying DHFR selection pressure;
(3) picking single clones;
(4) expanding the clones;
(5) producing antibodies from the clones;
(6) analyzing glycosylation of the antibodies produced from the clones; and (7) selecting a clone that produces an antibody wherein the heavy chain constant domains are glycosylated with a sugar chain at Asn297, wherein the sugar chain comprises at least 99% fucose, wherein if the sugar chain comprises N-glycolylneuraminic acid then the amount of N-glycolylneuraminic acid is 1% or less of the sugar chain and wherein if the sugar chain comprises N-terminal alpha-1,3-galactose then the amount of N-terminal alpha-1,3-galactose is 1% or less of the sugar chain.

* * * * *